United States Patent [19]

Boden et al.

[11] 4,430,233
[45] Feb. 7, 1984

[54] BRANCHED CHAIN KETONES AND USES THEREOF IN AUGMENTING OR ENHANCING THE AROMA OF PERFUMES, COLOGNES AND PERFUMED ARTICLES AND THE PROCESS FOR PREPARING SAME

[75] Inventors: Richard M. Boden, Monmouth Beach; Theodore J. Tyszkiewicz, Sayreville, both of N.J.

[73] Assignee: International Flavors & Fragrances Inc., New York, N.Y.

[21] Appl. No.: 384,960

[22] Filed: Jun. 4, 1982

Related U.S. Application Data

[62] Division of Ser. No. 296,868, Aug. 27, 1981, Pat. No. 4,374,276.

[51] Int. Cl.³ .............................................. D06M 13/20
[52] U.S. Cl. .................................................... 252/8.6
[58] Field of Search ........................................ 252/816

[56] References Cited

U.S. PATENT DOCUMENTS

| | | | |
|---|---|---|---|
| 2,315,046 | 3/1943 | Byrns | 568/397 |
| 2,463,742 | 11/1945 | Byrns | 568/398 |
| 4,321,255 | 3/1982 | Boden | 568/417 |

*Primary Examiner*—Maria Parrish Tungol
*Attorney, Agent, or Firm*—Arthur L. Liberman

[57] ABSTRACT

Described are acylated derivatives of triisobutylene defined according to the generic structures:

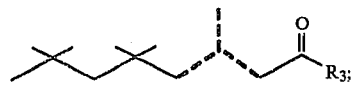

-continued

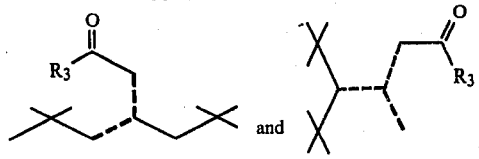

wherein, in each of the molecules one of the dashed lines represents a carbon-carbon double bond and each of the other of the dashed lines represents a carbon-carbon single bond; and wherein, in each of the molecules $R_3$ represents methyl or ethyl; uses thereof in augmenting or enhancing the aroma of perfume compositions, colognes and perfumed articles (e.g., solid or liquid anionic, cationic, nonionic, zwitterionic detergents, cosmetic powders, hair sprays and the-like) as well as processes for preparing same by first trimerizing isobutylene to form one or more compounds defined according to at least one of the structures:

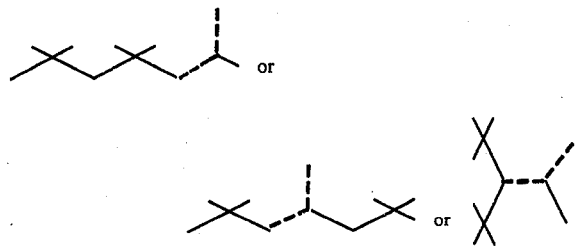

wherein in each of the molecules one of the dashed lines represents a carbon-carbon double bond and each of the other dashed lines represent carbon-carbon single bonds; and then reacting one or more of these trimerized isobutylene derivatives with an acyl anhydride having the structure:

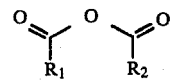

wherein, $R_1$ and $R_2$ are the same or different and each represents methyl or ethyl in the presence of a Lewis acid catalyst such as boron trifluoride etherate or stannic chloride thereby forming the acylated branched chain ketones of our invention defined according to at least one of the structures:
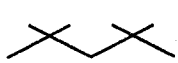 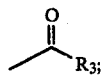
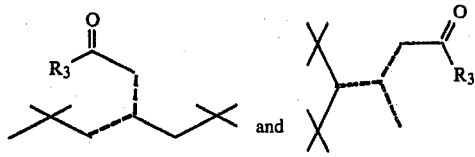
1 Claim, 16 Drawing Figures

GLC PROFILE FOR EXAMPLE A

GLC PROFILE FOR EXAMPLE I. REACTION PRODUCT

GLC PROFILE FOR EXAMPLE B.

GLC PROFILE FOR EXAMPLE I OF FRACTION 7.

NMR SPECTRUM FOR EXAMPLE B

IR SPECTRUM FOR EXAMPLE B.

NMR SPECTRUM FOR FRACTION 7 OF EX. I

IR SPECTRUM FOR FRACTION 7 OF EXAMPLE I.

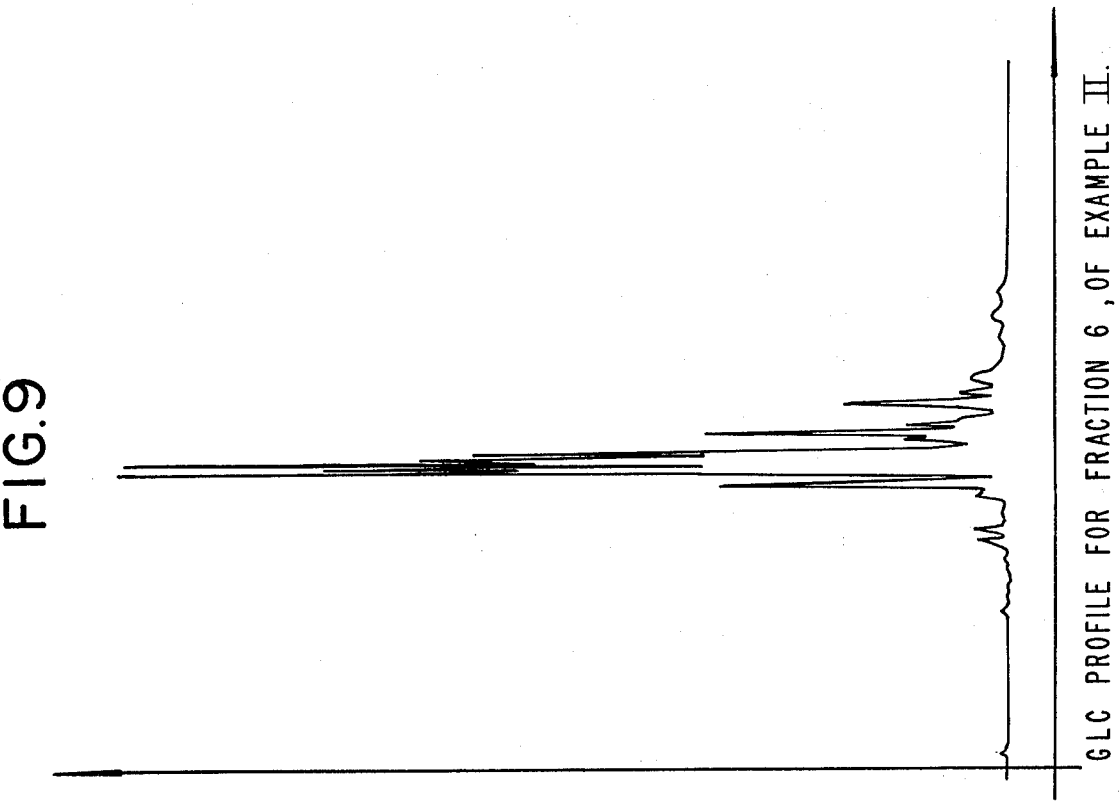
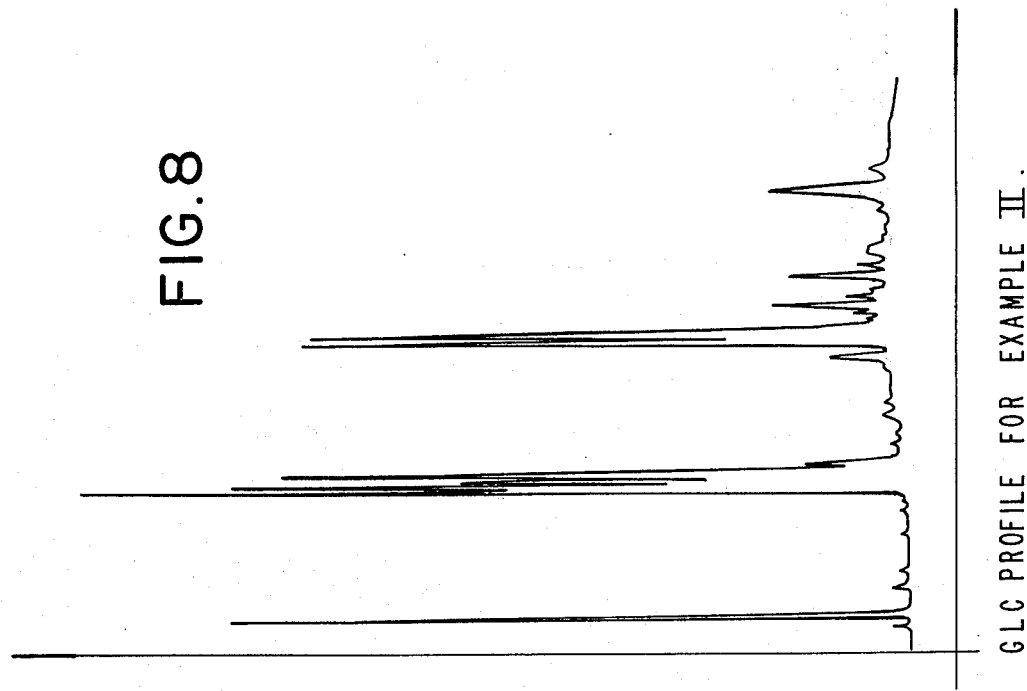

NMR SPECTRUM FOR FRACTION 6 OF EXAMPLE II.

IR SPECTRUM FOR FRACTION 6 OF EXAMPLE II.

GLC PROFILE FOR EXAMPLE III.
REACTION PRODUCT

GLC PROFILE FOR FRACTION 4 OF
EXAMPLE III.

NMR SPECTRUM FOR FRACTION 4 OF EXAMPLE III.

IR SPECTRUM FOR FRACTION 4 OF EXAMPLE III.

BRANCHED CHAIN KETONES AND USES THEREOF IN AUGMENTING OR ENHANCING THE AROMA OF PERFUMES, COLOGNES AND PERFUMED ARTICLES AND THE PROCESS FOR PREPARING SAME

This is a divisional of application Ser. No. 296,868, filed Aug. 27, 1981, now U.S. Pat. No. 4,374,276.

BACKGROUND OF THE INVENTION

The art of perfumery, having its origins in antiquity, has until very recent times relied predominantly on natural perfume essence oils for its pallette. Rapidly expanding population in modern times with concomitant changes in economic patterns and land used have made an unfavorable environment for the cultivation of essential oil crops. This has resulted in an increasingly sporadic, uneconomic, and insufficient supply of natural fragrance oils. As a result, the modern perfumer has devoted much of his time to replacing natural materials with synthesized raw materials which can be produced in both consistent quality and controllable cost from petrochemicals.

As aspect which has presented a problem to the perfumers while using synthetic raw materials is that of duplicating the rounded (blended) and full bodied effect of natural essential oils. These materials are normally quite complex with respect to trace ingredients which more often than not make important contributions to the odor profile, augmenting the odor strength, and blending the odor profile of the constituents. Accordingly, there is a continued search, which is especially evident within the last decade, for materials of unique odor character which can lend novel effects to modern perfumes and provide "lift" and strength enhancement sought with perfumes containing dominant proportions of petrochemically based raw materials.

The art of perfumery having its origins in antiquity has until very recent times relied predominently on natural perfume essence oils for its pallete. Rapidly expanding population in modern times with concomentent changes in economic patterns and land use have made an unfavorable environment for the cultivation of certain essential oil crops. This has resulted in an increasingly sparatic uneconomic and insufficient supply of natural fragrance oils. As a result, the modern perfumer has devoted much of his time to replacing natural materials with synthetized raw materials which can be produced in both consistent quality and controllable costs from petrochemicals.

An aspect which has presented a problem to the perfumers are utilizing synthetic raw materials as that of duplicating the rounded (blended) and full bodied effect of natural essential oils. These materials are normally quite complex with respect to trace ingredients which more often than not make important contributions to the odor profile, augmenting the odor strength and blending the odor profile of the constituents. Accordingly there are the continued search which is especially evident within the last decade for materials of unique odor character which can lend a novel effect to modern perfumes and provide "lift" and strength enhancement sought with perfumes containing doment proportions of petrochemically base raw materials.

One source of such petrochemically based raw materials is isobutylene having the structure:

which in its conversion to fuel products gives rise to side products which are trimers, commonly called "triisobutylene" but which have structures defined according to the generic structures:

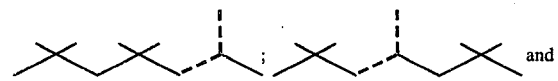

wherein each of the generic structures set forth above, in each of the molecules, one of the dashed lines represents a carbon-carbon double bond and each of the other of the dashed lines represent carbon-carbon single bonds.

The instant invention relates to reacting one or more of these "triisobutylene" derivatives which are produced by trimerization of isobutylene having the structure:

with an acylating agent, more particularly with an acyl anhydride defined according to the generic structure:

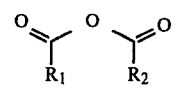

where $R_1$ and $R_2$ are the same or different and each represents methyl or ethyl.

The use of petroleum feedstocks as precusors for producing perfumery products is known in the prior art.

Thus, for example, U.S. Pat. No. 4,219,450 issued on Aug. 26, 1980 discloses the utilization of oximes of propene trimers and propere tetramers for augmenting or enhancing the aromas of colognes, perfumes and perfumed articles including detergents and cosmetics. It is indicated that these propene trimers are defined according to the structure:

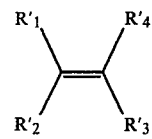

wherein $R_1'$ $R_2'$ $R_3'$ and $R_4'$ represent hydrogen or aliphatic hydrocarbon articles having from 1 up to 7 carbon atoms with the total number of carbon atoms among $R_1'$, $R_2'$, $R_3'$, and $R_4'$ being 7 or being 10 (the 7 in a case of a propane trimer and the 10 being in the case of a propane tetramer. However, the propane trimer and the propane tetramer oximes of U.S. Pat. No. 4,219,450 are indicated to be produced in a rather complex manner by first forming the propane trimer or propane tetramer epoxide; then reacting the resulting epoxide with activated clay to rearrange same to produce the propane trimer or propane tetramer ketone; and finally reacting the resulting ketone with hydroxlamine hydrochloride to produce the propane trimer or propane tetramer oxime. Indeed the creation of the propane trimer or propane tetramer epoxide requires the use of proxy compounds such as peracetic acid. Both the oximation step and the epoxidation step require great care in view of the danger of explosions capable of occurring during these processing steps.

Unsaturated ketones including unsaturated branched aliphatic acyclic ketones are well known for use for augmenting or enhancing the aroma and/or taste of consumable materials. Thus, Arctander, "Perfume & Flavor Chemicals (Aroma Chemicals)", published 1969, discloses at monograph No. 472, the use of butylidene acetone having the structure:

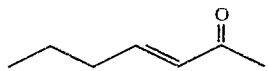

Arctander states that butylidene acetone has a powerful, grassy, green pungent odor and a rather poor tenacity. At monograph 2427, Vol. 2 Arctander states that Octylidene acetone having the structure:

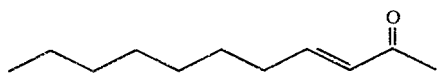

is useful in Jasmin compositions as a modifier for Amylcinnamic aldehyde, or in Gardenia and other heavy floral perfumes, where herbaceous-fruity notes are desirable and compatible with the fragrance picture.

U.S. Pat. No. 2,315,046 discloses the use as ingredients in perfumery of certain acylated olefins, which olefins have structures such as:

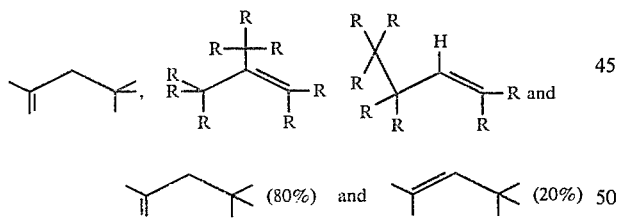

These materials are prepared interalia from commerical diisobutylene according to the reaction:

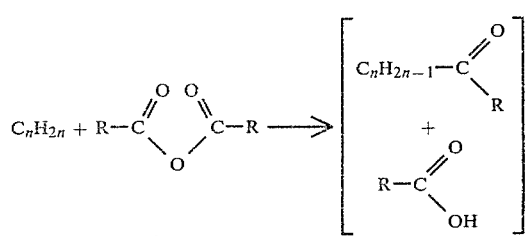

wherein n is 3 or more, and R represents a hydrocarbon radical. radical. Branched unsaturated alpha-beta ketones were known prior to that, for example in U.S. Pat. No. 2,246,032, issued on June 17, 1941, diclosing compounds having the generic structure:

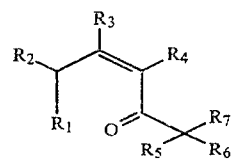

wherein $R_1$–$R_7$ may be any member of a group consisting of hydrogen, aliphatic and cyclo praffinic.

Also claimed in U.S. Pat. No. 2,315,046 are compounds having the structure:

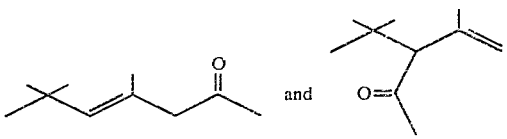

In addition, U.S. Pat. No. 2,463,742 discloses the reaction:

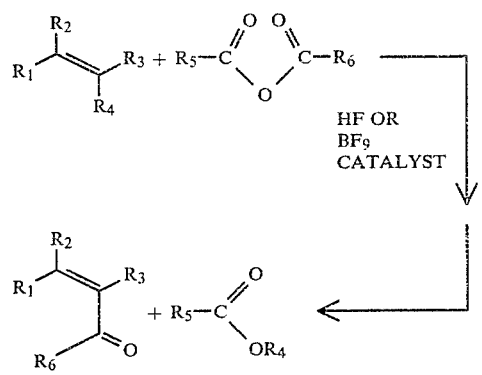

U.S. Pat. No. 3,453,317, issued on July 1, 1969, discloses certain gamma, delta unsaturated ketones as odorants for perfumery purposes at Columnn 4, line 33 including the group of ketones having the structures:

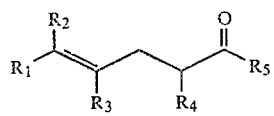

wherein $R_1$–$R_5$ are various hydrocarbon radicals.

U.S. Pat. No. 2,870,210, discloses as having aromas such as fruity, "reminiscent of apple juice" the compound 6,8-dimethyl-5-nonene-2-one having the structure:

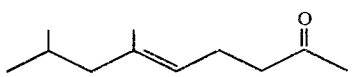

as well as 6,10-dimethyl-5-undecane-2-one having the structure:

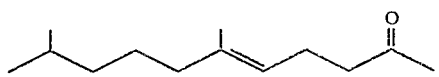

Since approximately 1960, International Flavors & Fragrances Inc. has been utilizing reaction products of acetic anhydride and triisobutylene in perfumery wherein the reaction takes place using a polyphosphoric acid catalyst. The preparation of the reaction product of acetic anhydride and triisobutylene in the presence of polyphosphoric acid is specifically set forth in Example "B", infra.

In comparing the organoleptic properties of the products prepared by reacting acetic anhydride with triisobutylene in the presence of polyphosphoric acid is the products prepared by reacting acetic or proprionic anhydride with triisobutylene in the presence of a Lewis acid catalyst, it is evident that the properties of the different materials are unexpectedly different from one another with each of the materials having their own specific advantages, depending upon whether the Lewis acid or protonic acid catalyst is used. Indeed as will be seen in the section entitled "Brief Description Of The Drawings", infra, the GLC profiles for the materials prepared using the Lewis acid catalyst in comparison to the materials prepared using the Lewis acid catalyst are quite different.

OBJECTS OF THE INVENTION

Accordingly, it is the object of this invention to provide new and useful synthetic chemical compounds derived from inexpensive petrochemical feedstocks particularly those feedstocks including a major amount of isobutylene.

Another object of our invention is to provide methods for preparing perfumery chemicals from derivatives of such inexpensive petroleum feedstocks particularly containing one or more triisobutylenes.

Yet another object of our invention is to provide perfume compositions and perfumed articles including but not limited to solid or liquid anionic, cationic, non-ionic or zwitterionic detergents containing as essential ingredients thereof one or more of the novel chemicals of this invention.

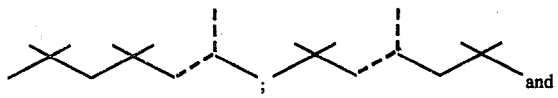

wherein in each of the molecules one of the dashed lines represents a carbon-carbon double bond and each of the other of the dashed lines represents a carbon-carbon single bond.

Figure 2:
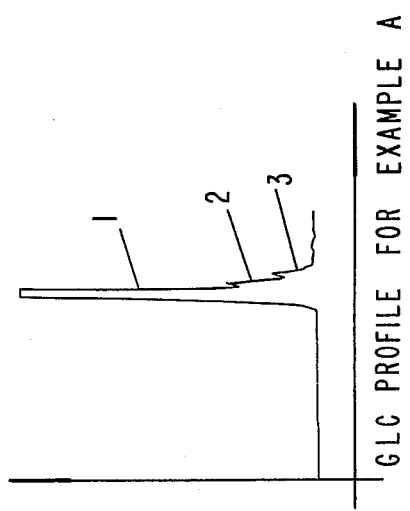

FIG. 2 is the GLC profile for the reaction product of triisobutylene and acetic anhydride in the presence of polyphosphoric acid prepared according to Example B.

Figure 3:
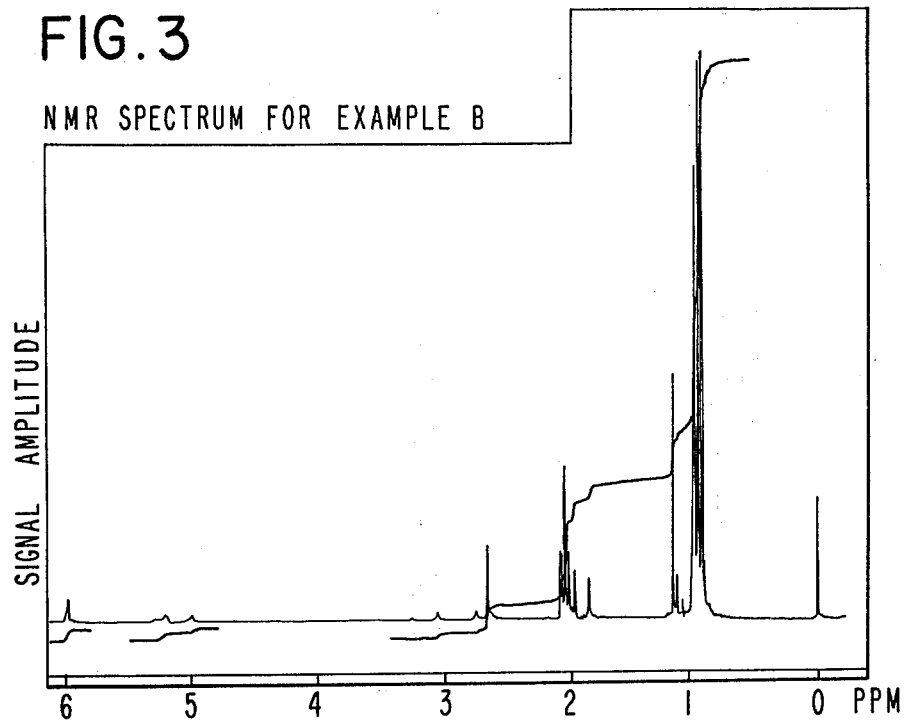

FIG. 3 is the NMR spectrum for the reaction product of triisobutylene and acetic anhydride in the presence of polyphosphoric acid prepared according to Example B.

Figure 4:
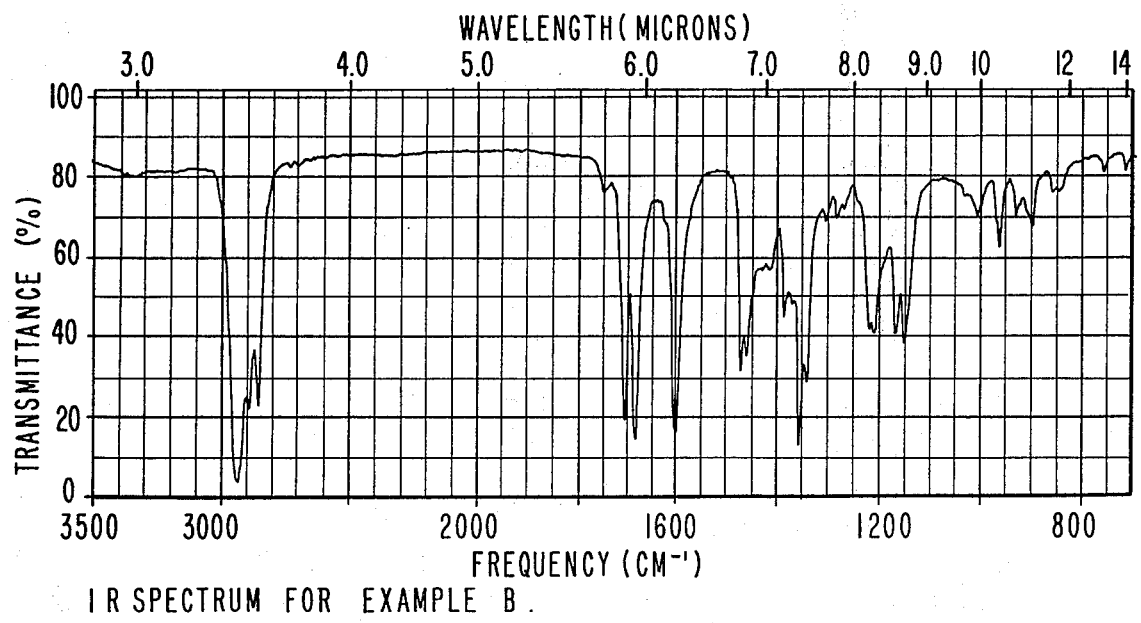

FIG. 4 is the infra-red spectrum for the reaction product of triisobutylene and acetic anhydride in the presence of polyphosphoric acid prepared according to Example B.

Figure 5A:
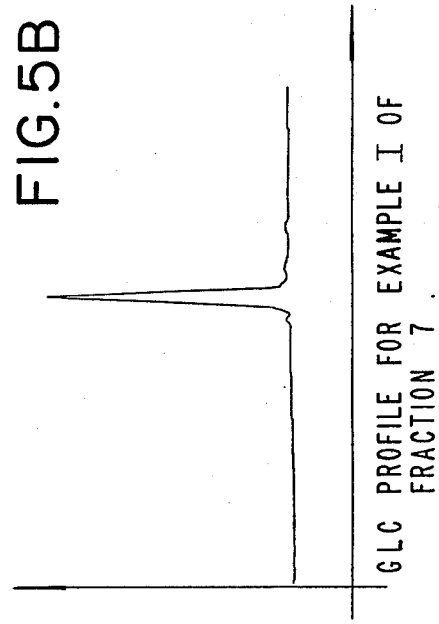

FIG. 5A is the GLC profile for the reaction product of Example I containing the compounds produced according to the reaction of triisobutylene with acetic anhydride in the presence of a boron trifluoride etherate catalyst containing the compounds having the structures:

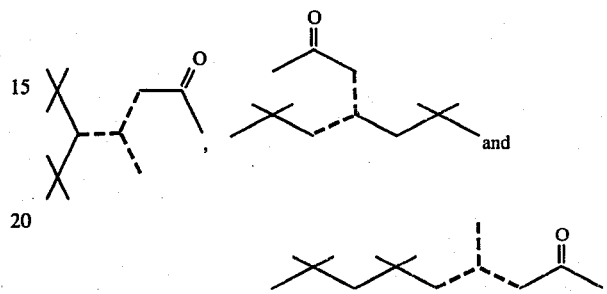

wherein in each of the molecules one of the dashed lines respresents a carbon-carbon double bond and each of the other of the dashed lines represent carbon-carbon single bonds.

Figure 5B:
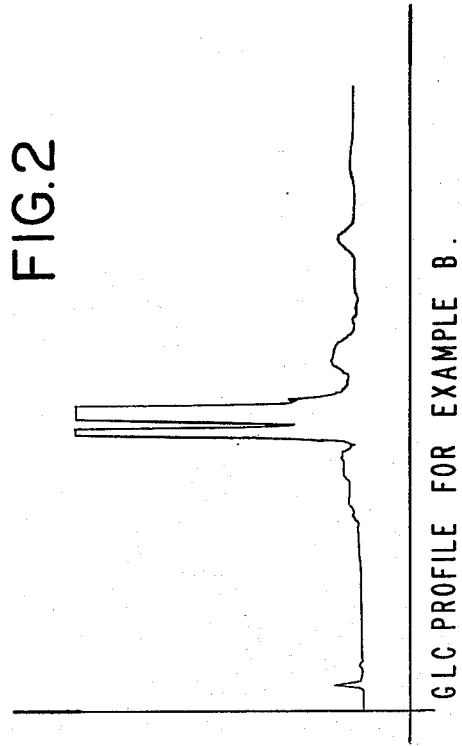

FIG. 5B is the GLC profile for fraction 7 of the distillation product of the reaction product of Example I containing the compounds having the structures:

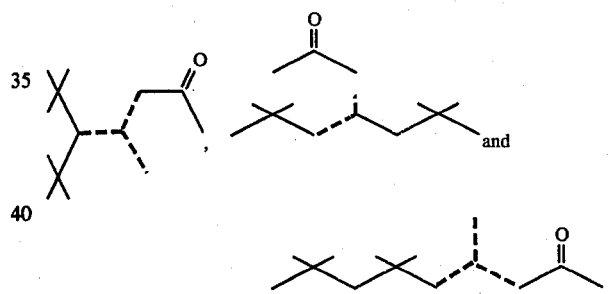

wherein in each of the molecules one of the dashed lines represents a carbon-carbon double bond and each of the other of the dashed lines represent carbon-carbon single bonds.

Figure 6:
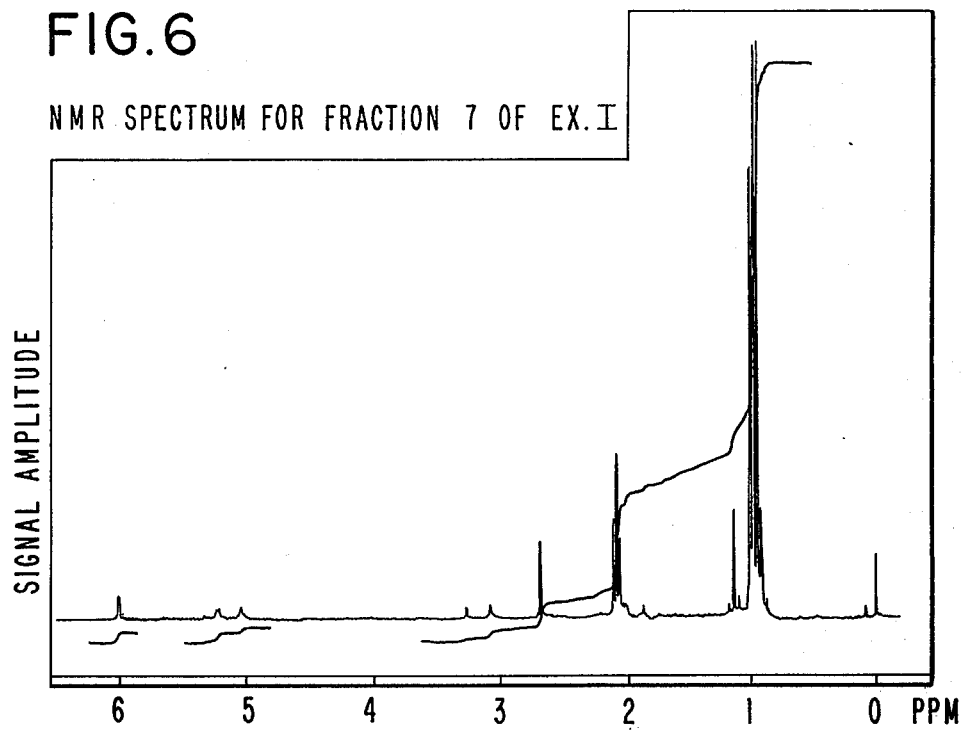

FIG. 6 is in the NMR spectrum for fraction 7 of the distillation product of the reaction product of Example I containing the compounds having the structure:

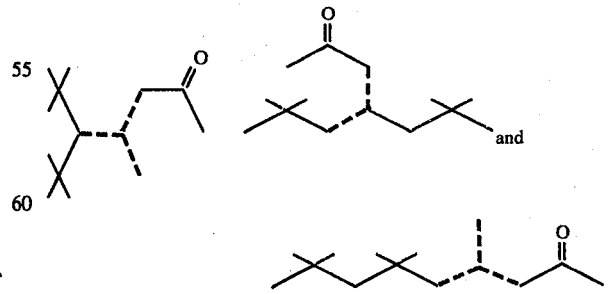

wherein in each of the molecules one of the dashed lines represents a carbon-carbon double bond and each of the other of the dashed lines represent carbon-carbon single bonds.

Figure 7:
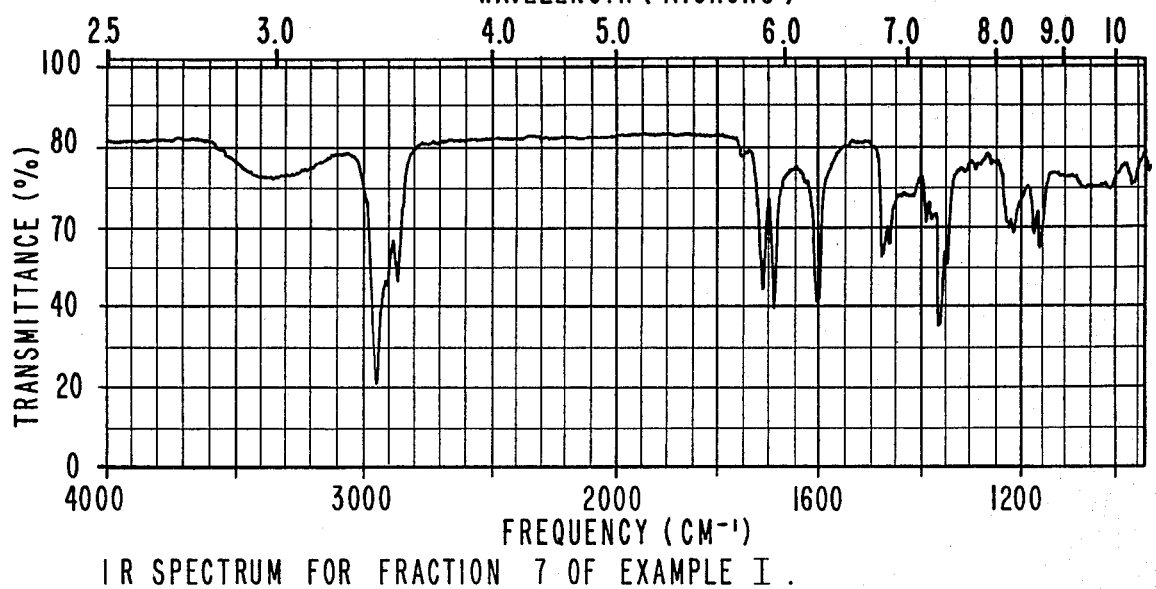

FIG. 7 is the infra-red spectrum for fraction 7 of the distillation product of the reaction product of Example I containing the compounds having the structures:

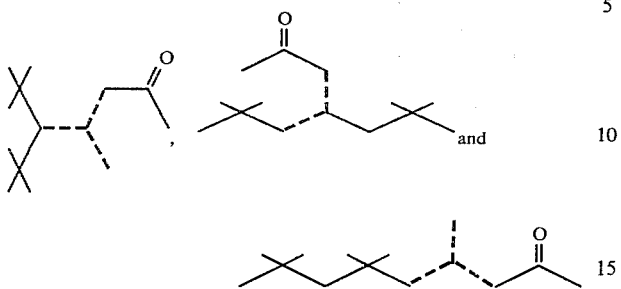

wherein in each of the molecules one of the dashed lines represents a carbon-carbon double bond and each of the other dashed lines represent a carbon-carbon single bonds.

FIG. 8 is the GLC profile for the reaction product of Example II produced by reaction of propionic anhydride with triisobutylene in the presence of a boron trifluoride etherate catalyst containing the compounds defined according to the structures:

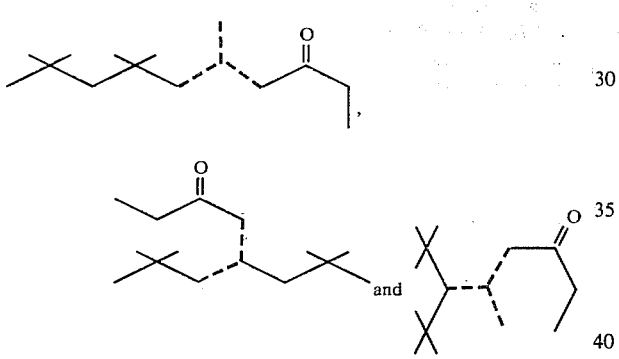

wherein in each of the molecules one of the dashed lines represents a carbon-carbon double bond and each of the other of the dashed lines represent carbon-carbon single bonds.

FIG. 9 is the GLC profile for fraction 6 of the distillation product of the reaction product of Example II containing the compounds having the structures:

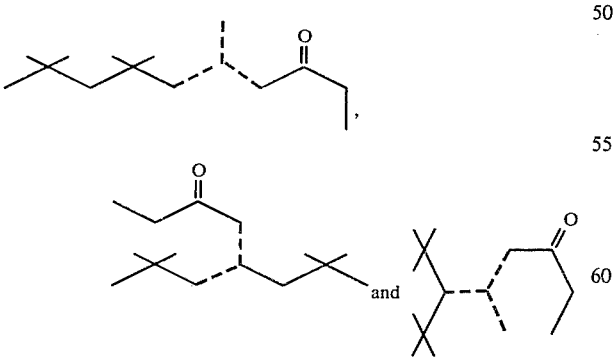

wherein in each of the molecules one of the dashed lines represents a carbon-carbon double bond and each of the other of the dashed lines represent carbon-carbon single bonds.

Figure 10:
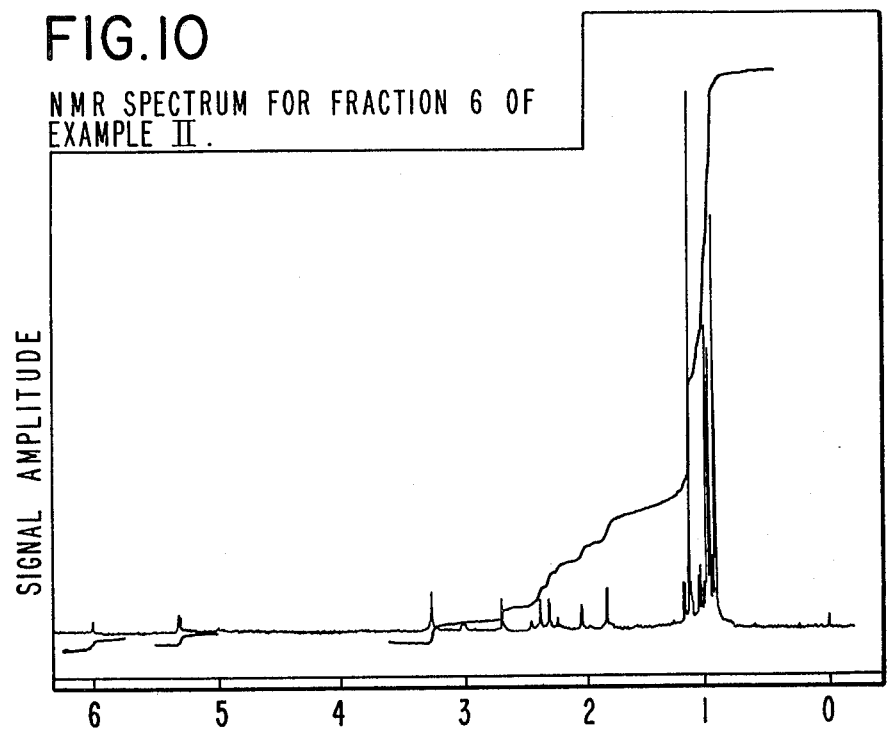

FIG. 10 is the NMR spectrum for fraction 6 of the distillation product of the reaction product of Example II containing the compounds having the structures:

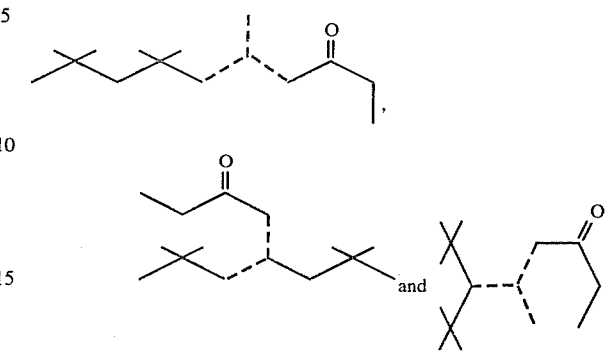

wherein in each of the molecules one of the dashed lines represents a carbon-carbon double bond and each of the other of the dashed lines represent carbon-carbon single bonds.

Figure 11:
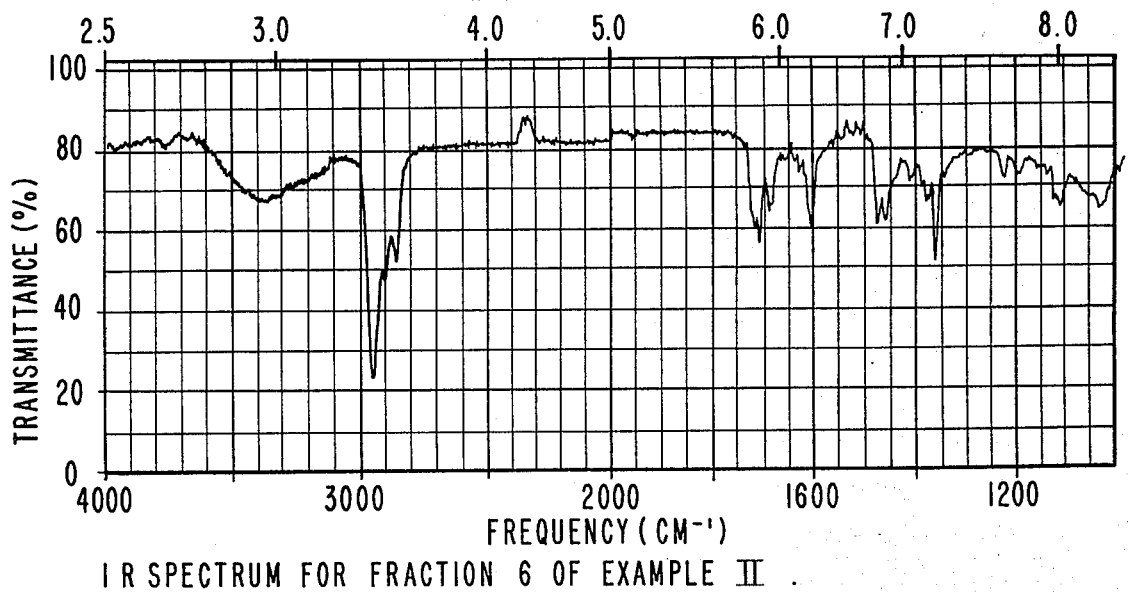

FIG. 11 is the infra-red spectrum for fraction 6 of the distillation product of the reaction product of Example II containing the compounds having the structures:

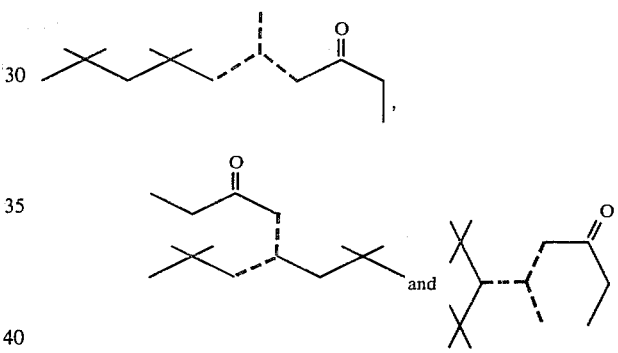

wherein in each of the molecules one of the dashed lines represents a carbon-carbon double bond and each of the other of the dashed lines represents carbon-carbon single bonds.

Figure 12A:
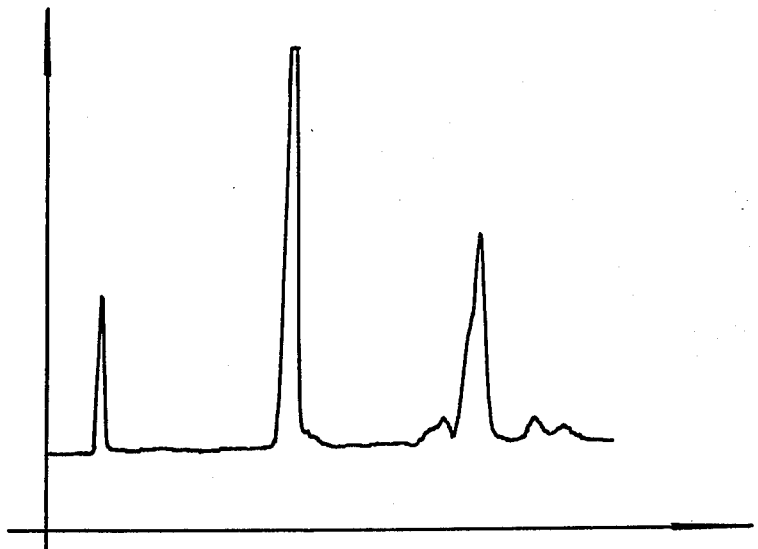

FIG. 12A is the GLC profile for the reaction product of Example III wherein the reaction between propionic anhydride and triisobutylene in the presence of a boron trifluoride etherate catalyst and which contains the compounds having having the structures:

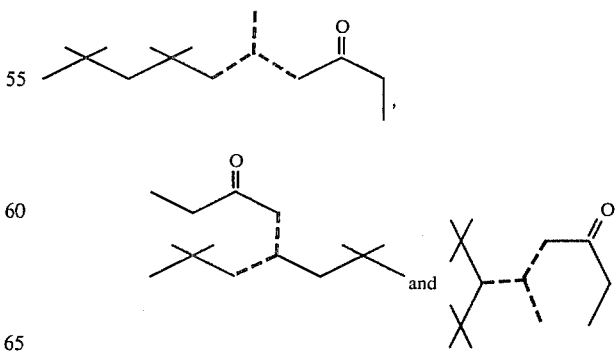

wherein in each of the molecules one of the dashed lines represents a carbon-carbon double bond and each of the other of the dashed lines represent a carbon-carbon single bonds.

Figure 12B:
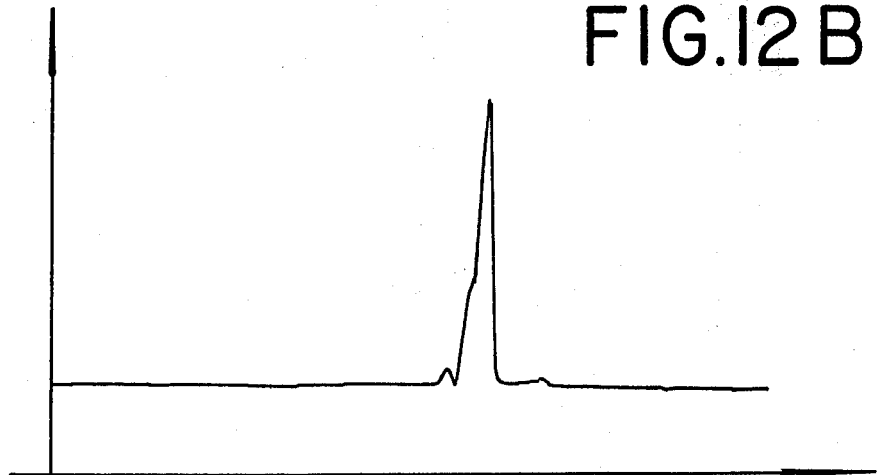

FIG. 12B is the GLC profile for Fraction 4 of the distillation product of the reaction product of Example III containing the compounds having the structures:

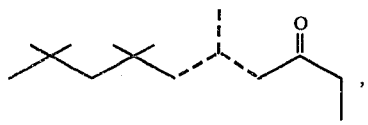

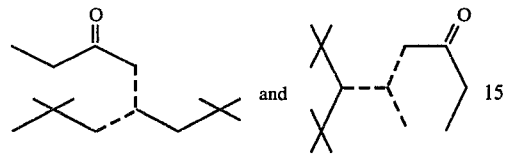

wherein in each of the molecules one of the dashed lines represents a carbon-carbon double bond and each of the other of the dashed lines represent a carbon-carbon single bonds.

Figure 13:
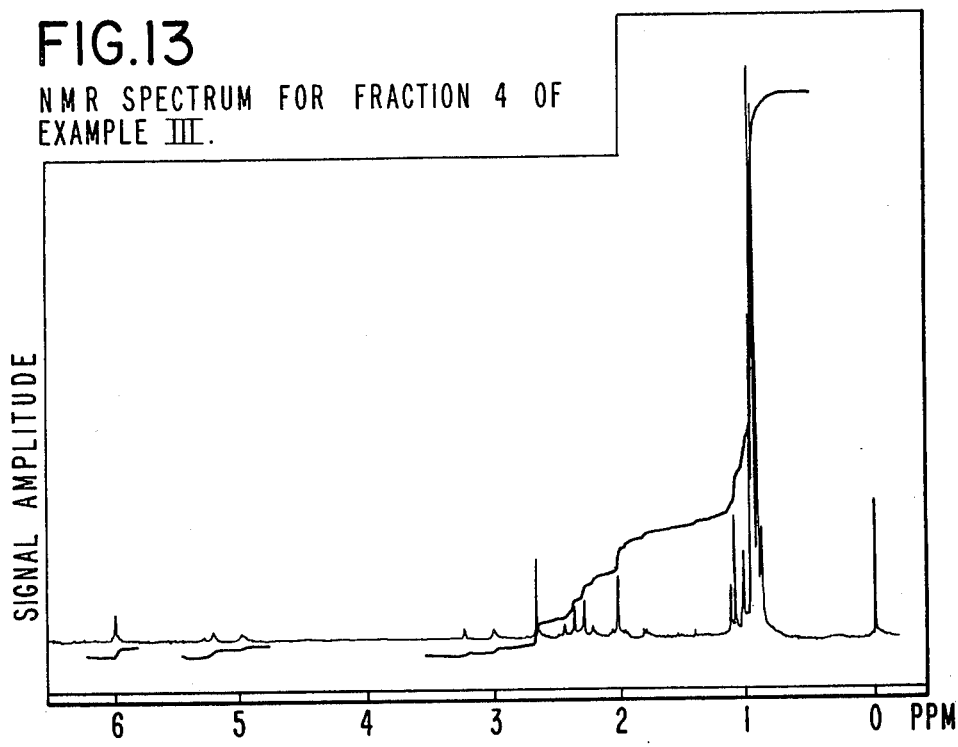

FIG. 13 is the NMR spectrum for fraction 4 of the distillation product of the reaction product of Example III containing the compounds having the structures:

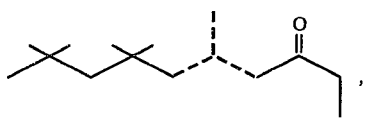

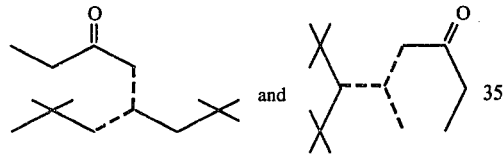

wherein in each of the molecules one of the dashed lines represents a carbon-carbon double bond and each of the other of the dashed lines represent carbon-carbon single bonds.

Figure 14:
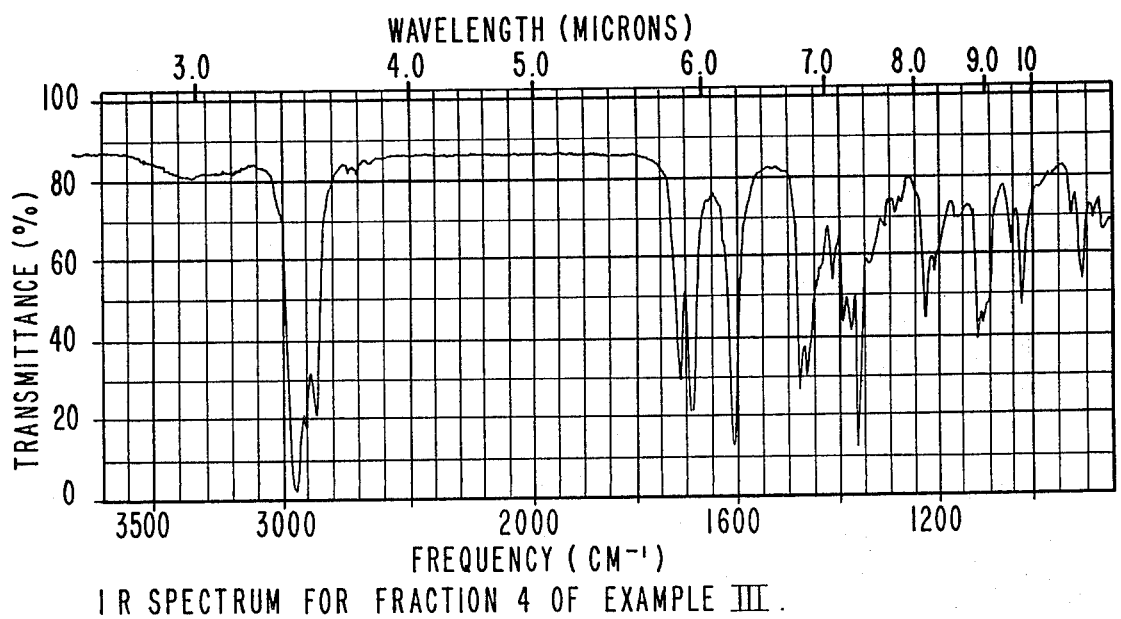

FIG. 14 is the infra-red spectrum for fraction 4 of the distillation product of the reaction product of Example III containing the compounds having the structures:

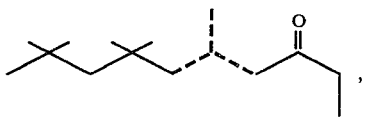

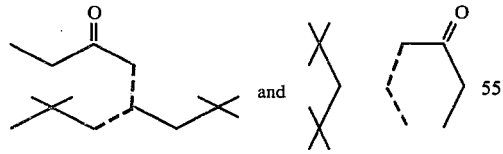

wherein in each of the molecules one of the dashed lines represents a carbon-carbon double bond and each of the other of the dashed lines represent carbon-carbon single bonds.

THE INVENTION

It has now been discovered that novel solid and liquid perfume compositions, colognes, and perfumed articles (e.g., solid or liquid anionic, cationic, nonionic and zwitterionic detergents; cosmetic powders; hair preparations; fabric softener compositions; and dryer-added fabric softener articles) having intense and long lasting ambery, fruity, ionone-like, winey, woody, sweet, orris-woody, and vetiver nuances with urine-like top notes and incense top notes may be provided by the utilization of one or more branched, acyclic unsaturated ketone derivatives defined according to one of the generic structures:

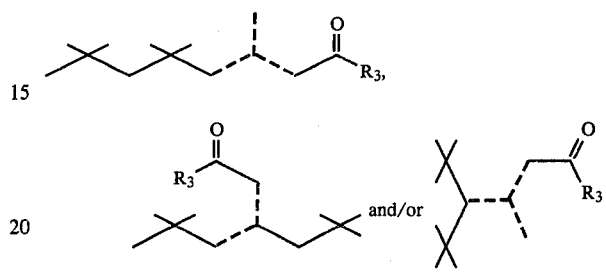

wherein $R_3$ represents ethyl or methyl and wherein in each of the molecules one of the dashed lines represents a carbon-carbon double bond and each of the other of the dashed lines represent carbon-carbon single bonds.

Unless otherwise specified, representation herein of carbon-carbon double bonds are intended to indicate a "cis" isomer, a "trans" isomer, or a mixture of "cis" and "trans" isomers with respect to that carbon-carbon double bond in the event that the carbon-carbon double bond is susceptible of such "cis-trans" isomerism.

The novel branched, unsaturated ketones of our invention may be prepared by first preparing triisobutylene as by trimerizing isobutylene according to the reaction:

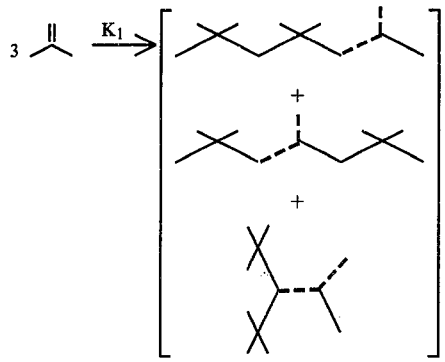

wherein $K_1$ represents the catalyst used in the trimerization and wherein in each of the molecules produced, one of the dashed lines represents a carbon-carbon double bond and each of the other of the dashed lines represent carbon-carbon single bonds.

The resulting triisobutylene material thus produced is used "as is" in the subsequent acylation reaction. Thus, for example, the subsequent acylation reaction may be carried out on the mixture of triisobutylene molecules according to the reaction:

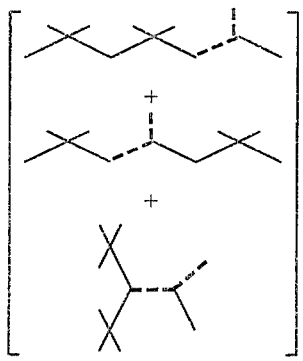

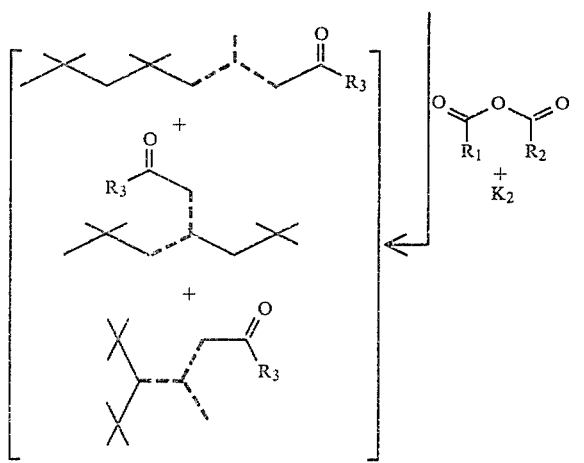

wherein $K_2$ represents the catalyst used; wherein $R_3$ is methyl or ethyl; wherein $R_1$ and $R_2$ are the same or different and each represents methyl or ethyl and wherein in each of the molecules of the reactant mixture and in each of the molecules of the mixture produced, one of the dashed lines represents a carbon-carbon double bond and each of the other of the dashed lines represent carbon-carbon single bonds. Obviously, in the situation wherein a mixed anhydride is used, that is wherein acetic-propionic anhydride is used as a reactant, a mixture of molecules will be produced wherein $R_3$ is both methyl and ethyl in a 50:50 proportion. Such a mixture has organoleptic properties combining the properties of both the mixture of molecules wherein $R_3$ is methyl and the mixture of molecules wherein $R_3$ is ethyl.

The particular Lewis acid catalyst used in the acylation reaction maybe boron trifluoride etherate, boron trifluoride, zinc chloride, aluminum chloride, zinc bromide, diethyl aluminum chloride, ethyl aluminum dichloride, stannic chloride or zinc bromide.

The temperature of reaction may vary between 0° C. and 80° C. with a preferred reaction temperature of 10° C. up to 50° C.

The mole ratio of trimer of isobutylene:acylating agent (e.g., acyl anhydride) may vary between 1:1.1 and 2:1.0, with a preferable mole ratio of isobutylene trimer::acylating agent being about 1:0.7. The acyl anhydrides which may be used are:

Acetic anhydride
Propionic anhydride
Acetic Propionic anhydride

The concentration of catalyst in the reaction mass may vary from 2.5 weight percent to 150 weight percent with a preferred Lewis acid concentration being between 5 and 10% by weight of the reaction mass.

Although an inert solvent may be used in the reaction mass (e.g., benzene, toluene, xylene, dichloromethane or 1,2-dichlorobenzene) it is preferred that no solvents be used, and that the reaction be carried out in the absence of solvent.

Although pressures greater than or less than atmospheric pressure may be used, no specific advantage is seen in using higher or lower pressures insofar as conversion, yield or time of reaction is concerned.

Accordingly, it is most preferred to use atmospheric pressure as a reaction condition.

The following table sets forth specific reaction products contemplated within the scope of our invention, and their individual organoleptic properties:

TABLE I

| Structures defining reaction product | Fragrance Properties |
|---|---|
| Mixture of compounds defined according to the structures: <br><br> prepared according to the process of Ex. I. | An ambery, fruity, ionone-like, winey and woody aroma profile |
| Mixture of compounds defined according to the structures: <br><br> prepared according to Ex. II or III. | A sweet woody aroma with a urine top note |

The unsaturated branched-chain ketone derivatives and one or more auxiliary perfume ingredients including for example hydrocarbon alcohol ketones (other than the unsaturated branched-chain ketone derivatives of our invention), aldehydes, nitriles, esters, lactones or cyclic esters, synthetic essential oils and natural essential oils may be admixed to that the combined odors of the individual components produce a pleasant and desired fragrance, particularly and preferably in the woody, and winey and/or fruity fragrance areas. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top notes which are usually low boiling fresh smelling materials.

In perfume composition, it is the individual components which contribute to their particular olfactory characteristics, however the over-all sensory effect of the perfume composition will be at least the sum total of the effects of each of the ingredients. Thus, one or more of the unsaturated branched-chain ketone derivative(s) of our invention can be used to alter, modify or enhance the aroma characteristics of a perfume composition, for example, by utilizing or moderating the olfactory reaction contributed by another ingredient in the composition.

The amount of unsaturated branched-chain ketone derivative(s) of our invention which will be effective in perfume compositions as well as in perfumed articles and colognes depends on many factors, including the other ingredients, their amounts and the effects which are desired. It has been found that perfume compositions containing as little as 0.01% of the unsaturated branched-chain ketone derivative(s) or even less (e.g., 0.005%) can be used to impart an ambery, fruity, ionone-like, winey, woody, sweet-woody aroma profile with urine-like top notes to soaps, cosmetics, detergents (including anionic, nonionic and cationic detergents) or other products. The amount employed can range up to 70% of the fragrance components and will depend on considerations of cost, nature of the end product, the effect desired on the finished product and the particular fragrance sought.

The unsaturated branched-chain ketone derivative(s) of our invention are useful (taken alone or together with other ingredients in perfume compositions) in detergents and soaps, space odorants and deodorants, perfumes, colognes, toilet water, bath preparations, such as lacquers, brillantines, pomades and shampoos; cosmetic preparations, such as creams, deodorants, hand lotions and sun screens; powders, such as talcs, dusting powders, face powders and the like. As little as 1% of the unsaturated branched-chain ketone derivative(s) will suffice to impart an intense ambery, fruity, ionone-like, winey, woody, sweet-woody aroma to woody and/or ambery perfume formulations. Generally, no more than 3% of the unsaturated branched-chain ketone derivative(s) based on the ultimate end product, is required in the perfume composition.

In addition, the perfume composition or fragrance composition of our invention can contain a vehicle, or carrier for the unsaturated branched-chain ketone derivative(s). The vehicle can be a liquid such as a non-toxic alcohol, a non-toxic glycol, or the like. The carrier can also be an absorbent solid, such as a gum (e.g., gum arabic), or components for encapsulating the composition (such as gelatin).

It will thus be apparent that the unsaturated branched-chain ketone derivative(s) of our invention can be utilized to alter, modify or enhance sensory properties, particularly organoleptic properties, such as flavor(s) and/or fragrance(s) of a wide variety of consumable materials.

The following Example A sets forth the procedures for preparing precursors of the compounds of our invention, the unsaturated branched-chain ketones.

The following Example B sets forth a procedure for preparing a prior art substance which is somewhat similar but not the same as the substances of our invention.

The following Examples I-III set forth procedures for preparing the unsaturated branched-chain ketones of our invention.

The remainder of the examples set forth the uses of the unsaturated branched-chain ketones of our invention for their organoleptic properties.

It will be understood that these examples are illustrative and that the invention is to be considered restricted thereto, only as indicated in the appended claims.

All parts and percentages given herein are by weight, unless otherwise specified.

EXAMPLE A

Preparation of Triisobutylene Derivatives

Reaction:

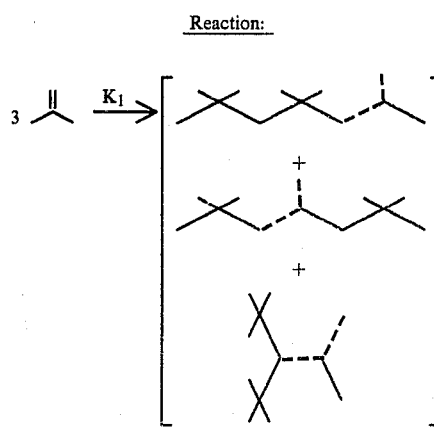

(wherein in each of the molecules indicated, one of the dashed lines is a carbon-carbon double bond and each of the other of the dashed lines is a carbon-carbon single bonds).

Triisobutylene is prepared according to one of the procedures set forth below:

(i) Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

(ii) U.S. Pat. No. 3,627,700, issued on Dec. 14, 1971, (Zuech)

(iii) U.S. Pat. No. 3,538,181, issued on Nov. 3, 1970, (Banks)

(iv) U.S. Pat. No. 3,461,184, issued on Aug. 12, 1969 (Hay, et al)

As an illustration, and not by way of limitation, the following example sets forth the preparation of triisobutylenes useful in producing the unsaturated branched-chain ketones which are useful in producing the fragrances of our invention.

Over a period of ten hours, 2-methyl-1-propene is pumped through a 5'×⅝" (0.625 inch) tube packed with 15.0 g of polystyrene sulfonic acid catalyst, at a temperature of 100° C. and at a pressure of 400 psig.

The resulting material is distilled in a fractionation column in order to separate the triisobutylene from the higher and lower molecular weight oligemers, which are formed during the reaction as by-products.

Figure 1:
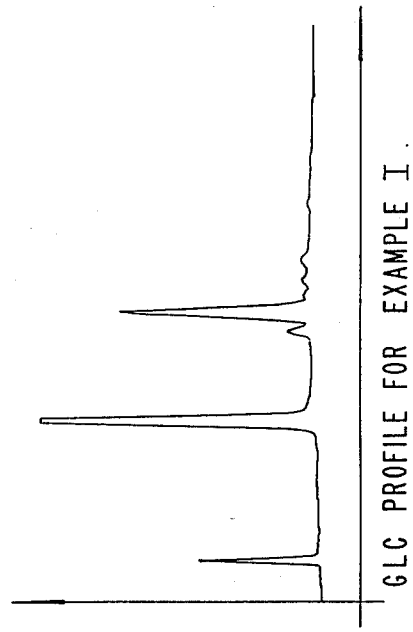
FIG. 1 is the GLC profile for triisobutylene prepared according to Example A, the reaction mixture containing compounds defined according to the generic structures.

FIG. 1 is the GLC profile for the reaction product containing a mixture of triisobutylenes which mixture contains the compounds defined according to the structures:

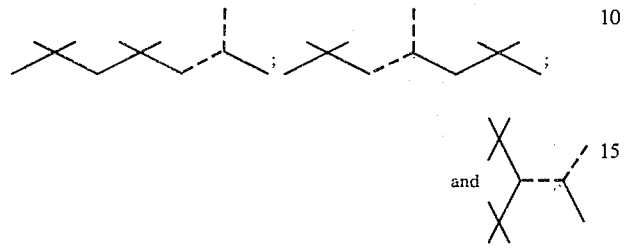

wherein in each of the molecules indicated one of the dashed lines is a carbon-carbon double bond and each of the other of the dashed lines represent a carbon-carbon single bond.

Peak 1 on FIG. 1 signifies the compound having the structure:

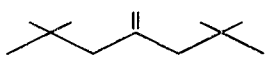

Peaks 2 and 3 of the FIG. 1 GLC profile indicate the compounds defined according to the structures:

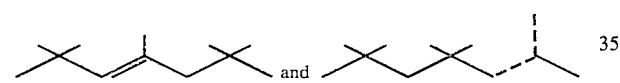

wherein in the molecules defined according to the structure:

one of the dashed lines represents a carbon-carbon double bond and the other of the dashed lines represent a carbon-carbon single bond.

The mixture produced according to the foregoing procedure is utilized in preparing the branched-chain unsaturated ketones of Example I, II and III, infra.

EXAMPLE B

Prior Art Preparation of Branched-Chain Unsaturated Ketones

Reaction:

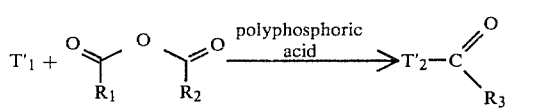

wherein $T_1'$ represents a mixture of triisobutylenes prepared according to the procedure of Example A and $T_2'$ represents a triisobutenyl moiety unlike the triisobutenyl moieties of the compounds prepared according to any of Examples I, II or III, infra; and wherein $R_1$, $R_2$ and $R_3$ each represent methyl.

Into a 22-liter flask equipped with stirrer, thermometer, reflux condenser and heating apparatus and addition funnel is placed acetic anhydride. The acetic anhydride is heated to 55°–60° C. Five percent by weight of the acetic anhydride, of polyphosphoric acid is charged to the acetic anhydride through the addition funnel over a period of 30 minutes. The reaction mass is then stirred and a quantity of triisobutylene prepared according to the procedure of Example A is added to the reaction mass from the addtion funnel over a period of 1 hour. The quantity of triisobutylene is in equimolar proportioned to the amount of acetic anhydride added. The reaction mass is then heated at 55°–60° C., with stirring over a period of 16 hours. The reaction mass is then added to an equal quantity of warm water and the reaction product is extracted with diethyl ether. The diethyl ether is evaporated from the extracted product and the reaction product is then fractionally distilled to yield a mixture of compounds which may be defined according to the structure:

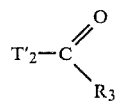

Organoleptic evaluation, GLC. NMR and IR analyses yield the information that the compounds defined according to the structure:

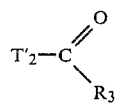

wherein T' is triisobutyl and $R_3$ is methyl are different in kind from the structures defined according to:

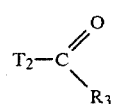

with structures produced according to Example I wherein $T_2$ is triisobutenyl as set forth on the "product" side of the reaction of Example I, infra and $R_3$ is methyl. In addition the organoleptic properties of the compounds having the structure:

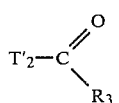

are different in kind from the organoleptic property to the compounds defined according to the structure:

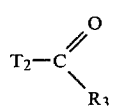

FIG. 2 is the GLC profile for the reaction product produced according to this example defined according to the structure:

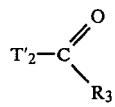

wherein T$_2'$ is triisobutenyl and R$_3$ is methyl.

FIG. 3 is the NMR spectrum for the reaction product defined according to the structure:

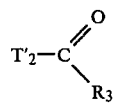

FIG. 4 is the infra-red spectrum for the reaction product defined according to the structure:

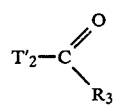

EXAMPLE I

Preparation of Acetyl Triisobutylene According to Invention

Reaction:

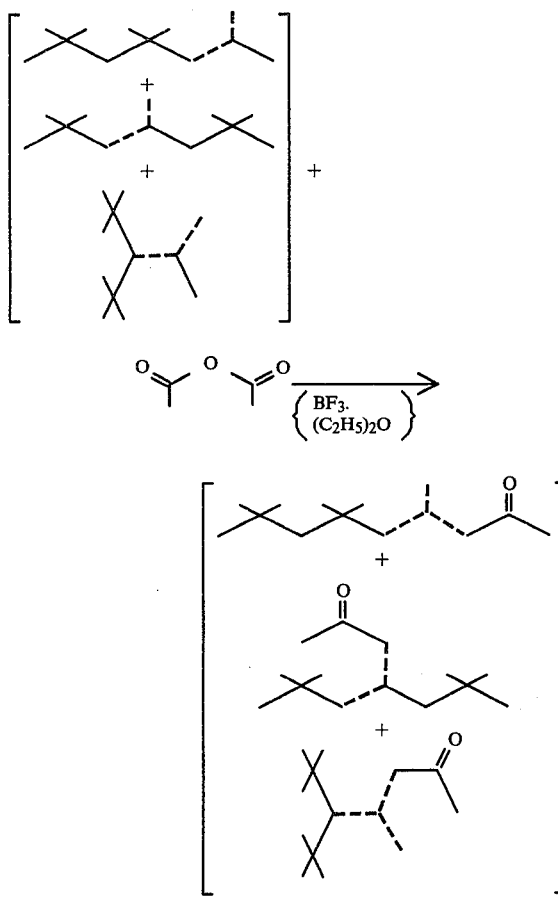

(wherein in each of the molecules of the reactant mixture and in each of the molecules of the reaction product one of the dashed lines represents a carbon-carbon double bond and each of the other of the dashed lines represent carbon-carbon single bonds).

Into a 12-liter reaction flask equipped with reflux condenser, addition funnel, thermometer, THERMOWATCH ® (a trademark owned by the Instruments for Research & Industry Company of 108 Franklin Avenue, Cheltenham, Pa.), heating mantle, and nitrogen blanket is placed 4200 grams of triisobutylene (25 moles) prepared according to Example A. To the triisobutylene is charged 1787 grams of acetic anhydride (17.5 moles). The reaction mass is heated 65° C. Over a period of 1.25 hours while maintaining the reaction mass of 59°–65° C., 248 grams (1.75 moles) of boron trifluoride etherate is slowly added to the reaction mass. The reaction mass is then stirred at a temperature of 65° C. for a period of 12 hours.

With cooling 4-liters of 12.5% sodium hydroxide solution (aqueous) is added to the reaction mass.

The reaction mass is then transferred to a separatory funnel and 4-liters of 12.5% aqueous sodium hydroxide is again added where upon the pH of the aqueous layer is 6 and the pH of the organic layer is 3. An additional 1-liter of 12.5% sodium hydroxide is added whereupon the pH of the aqueous layer is 12.

The organic layer is then washed with 2-liter aliquots of saturated sodium chloride until the pH thereof is 7.

The organic layer is distilled on a 2 inch splash column packed with stones yielding the following fractions:

| Fraction No. | Vapor Temp. | Liquid Temp. | Head Vac. mm. Hg. |
|---|---|---|---|
| 1 | 24/59 | 37/71 | 12/5 |
| 2 | 65 | 82 | 5. |
| 3 | 93 | 103 | 5. |
| 4 | 107 | 137 | 2.8 |
| 5 | 105 | 170 | 2.8 | which is indicated to be on a 2" splash column stones.

Fraction 2 contains 93% recover triisobutylene.
Fraction 3 contains 85% recover triisobutylene.
Fraction 4 contains 26% recover triisobutylene.
Fraction 3 and 4 are then both for redistillation (weight 1,666 grams).

The redistillation is on a 1 foot Goodloe column and yields the following fractions:

| Fraction No. | Vapor Temp. | Liquid Temp. | Head Vac. mm. Hg. | Reflux Ratio R/D | Weight Fract. |
|---|---|---|---|---|---|
| 1 | 90/70 | 86/93 | 5/4.4 | 1.1/4:1 | 175 |
| 2 | 73 | 96 | 3.0 | 4:1 | 180 |
| 3 | 73 | 96 | 3.0 | 4:1 | 182 |
| 4 | 73 | 98 | 3.0 | 4:1 | 195 |
| 5 | 73 | 99 | 3.0 | 4:1 | 130 |
| 6 | 71/72 | 94/100 | 3.0 | 1.1/1:1 | 185 |
| 7 | 74 | 100 | 3.0 | 1:1 | 210 |
| 8 | 75 | 104 | 3.0 | 1:1 | 211 |
| 9 | 98 | 184 | 3.0 | 1:1 | 166 |

FIG. 5A is the GLC profile for the reaction product prior to the first distillation (conditions: 12% SF 96 column programmed at 100°–220° C. at 8° C. per minute; dimensions of columns 6'×¼").

FIG. 5B is the GLC profile for Fraction 7 of the foregoing distillation (conditions: 12% SF 96 column; 6'×¼"; programed at 100°–220° C. at 8° C. per minute).

FIG. 6 is the NMR spectrum for Fraction 7 of the foregoing distillation.

FIG. 7 is the infra-red spectrum for Fraction 7 of the foregoing distillation.

EXAMPLE II

Preparation of Propionyl Triisobutylene

Reaction:

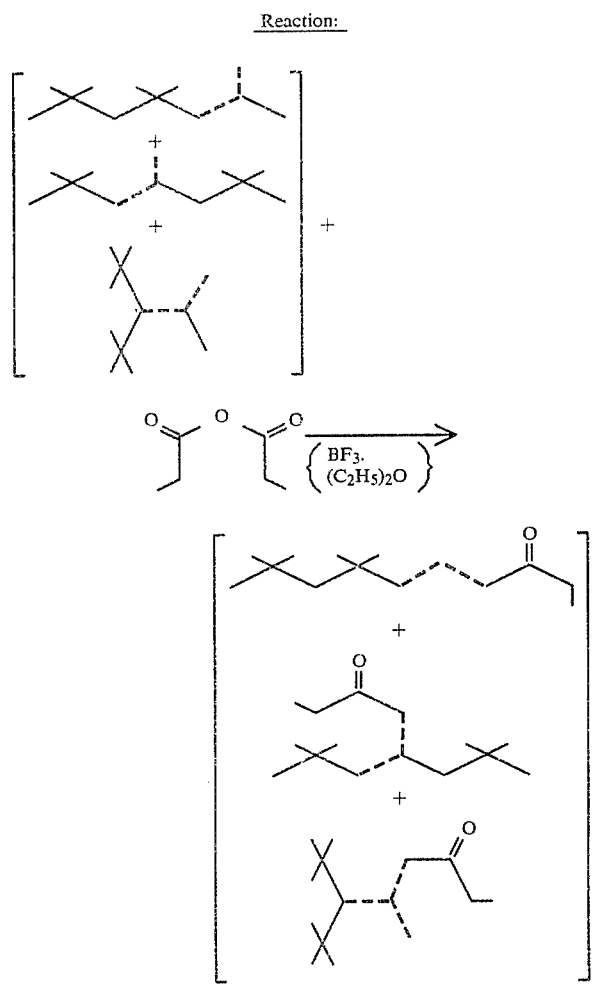

(wherein in each of the molecules reacted and in each of the molecules produced, one of the dashed lines represents a carbon-carbon double bond and each of the other of the dashed lines represent carbon-carbon single bonds).

Into a 500 ml reaction flask equipped with reflux condenser, addition funnel, thermometer, Thermowatch® apparatus, heating mantle and nitrogen blanket apparatus is placed 154.9 grams (1.19 moles) of proprionic anhydride and 15.9 ml (0.119 moles) of boron trifluoride etherate. While the resulting mixture is at 24° C., through the addition funnel, 194 grams (1.19 moles) of triisobutylene prepared according to Example A is added over a period of 35 minutes while maintaining the reaction mixture temperature at 25°–26° C. The reaction mass is then heated up to 65° C. and the reaction mass is maintained at 65° C. for a period of 10 hours.

At the end of the 10 hour period the reaction mass is poured into a 2-liter separatory funnel and 100 ml of 50% aqueous sodium hydroxide is added. The resulting product is then cooled to room temperature and the lower aqueous phase is removed from the upper organic phase. The organic phase is then washed with two 300 ml portions of saturated sodium chloride solution. The reaction mass is then distilled on a microvigreux column yielding the following fractions:

| No. | Vapor Temp | Liquid Temp. | Head Vac. mm.Hg | Weight Fraction |
|---|---|---|---|---|
| 1 | 37/32 | 43/34 | 3/3 | 25 |
| 2 | 34 | 39 | 3 | 26 |
| 3 | 34 | 43 | 3 | 41 |
| 4 | 43 | 70 | 3 | 41 |
| 5 | 86 | 97 | 3 | 7 |
| 6 | 104 | 120 | 3 | 24 |
| 7 | 130 | 160 | 3 | 12 |
| 8 | 165 | 220 | 3 | 6 |

FIG. 8 is the GLC profile for the reaction product prior to distillation.

FIG. 9 is the GLC profile for Fraction 6 of the foregoing distillation.

FIG. 10 is the NMR spectrum for Fraction 6 of the foregoing distillation.

FIG. 11 is the infra-red spectrum for Fraction 6 of the foregoing distillation.

EXAMPLE III

Preparation of propionyl Triisobutylene

Reaction:

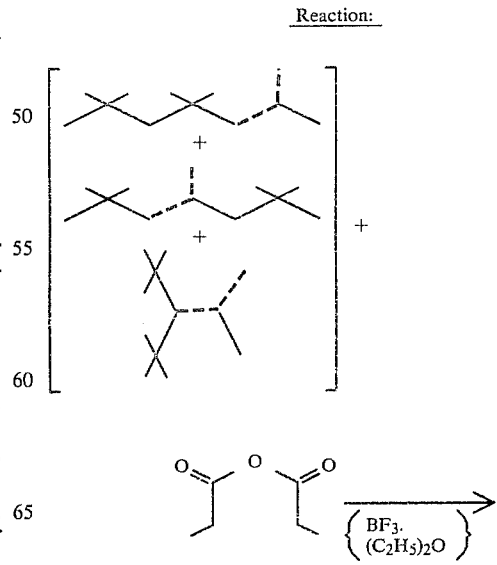

-continued
Reaction:

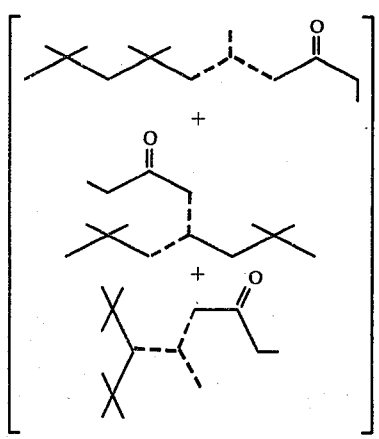

(wherein in each of the molecules produced and in each of the molecules reacted one of the dashed lines represents a carbon-carbon double bond and the other of the dashed lines represent carbon-carbon single bonds.

Into a 12-liter reaction flask equipped with reflux condenser additional funnel thermowatch apparatus heating mantle and nitrogen blanket apparatus is placed 5,536 ml (4208 grams) of triisobutylene (25.0 moles) prepared according to Example A. 2,277 grams (17.5 moles) of propionic anhydride is then added to the reaction mass. The reaction mass is heated to 60° C. and that the temperature of 60° C. over a period of 1 hour 745 grams (5.25 moles) of boron trifluoride etherate is added to the reaction mass. The reaction mass is then continued to be heated at 65°–66° C. for a period of 8.5 hours.

The reaction mass is then transferred to separatory funnel and the organic layer is washed as follows:
(a) 3-liters of water
(b) Two 2-liter portions of 12% aqueous sodium hydroxide
(c) Two 4-liter portions of saturated sodium chloride
the organic phase is then dryed over anhydrous magnesium sulfide and distilled on a 2" splashed column packed with stones to yield the following fractions:

| Fraction No. | Vapor Temp. | Liquid Temp. | Head Vac. mm.Hg. |
|---|---|---|---|
| 1 | 25/57 | 45/67 | 8/3.6 |
| 2 | 56 | 70 | 3.2 |
| 3 | 61 | 80 | 3.1 |
| 4 | 74 | 94 | 3.1 |
| 5 | 88 | 100 | 2.5 |
| 6 | 98 | 112 | 2.2 |
| 7 | 100 | 123 | 2.0 |
| 8 | 134 | 165 | 3.4 |

Fraction 1 contains 97% recovered triisobutylene.
Fraction 2 contains 97% recovered triisobutylene.
Fraction 3 contains 93% recovered triisobutylene.
Fraction 4 contains 84% recovered triisobutylene.
Fractions 5, 6 and 7 are bulked and redistilled on a 1" Goodloe column yielding the following fractions:

| Fraction No. | Vapor Temp. | Liquid Temp. | Head Vac. mm.Hg. | Reflux Ratio R/D | Weight Fract. |
|---|---|---|---|---|---|
| 1 | 31/78 | 92/103 | 3/2.7 | 1:1/4:1 | 157 |
| 2 | 83 | 103 | 2.7 | 4:1 | 215 |
| 3 | 83 | 103 | 2.7 | 4:1 | 185 |
| 4 | 88 | 103 | 2.0 | 4:1 | 85 |
| 5 | 82 | 101 | 2.2 | 4:1 | 162 |
| 6 | 84 | 109 | 2.2 | 4:1 | 176 |
| 7 | 85/91 | 103/104 | 0/3.2 | 1:1/1:1 | 210 |
| 8 | 91 | 105 | 3.0 | 3:0 | 205 |
| 9 | 101 | 120 | 2.8 | 1:1 | 48 |
| 10 | 105 | 135 | 2.8 | 1:1 | 62 |

Fractions 2–9 are bulked.

FIG. 12A is a GLC profile for the reaction product prior to distillation (conditions: SF 96 column, 6'×¼"; programmed at 100°–220° C. at 8° C. per minute).

FIG. 12B is the GLC profile for Fraction 4 of the foregoing distillation (conditions: 100°–220° C. at 8° C. per minute; SF-96 column; 6'×¼" column).

FIG. 13 is the NMR spectrum for Fraction 5 of the foregoing distillation.

FIG. 14 is the infra-red spectrum for Fraction 4 of the foregoing distillation.

EXAMPLE IV

Woody Perfume Compositions

The unsaturated branched-chain ketones produced according to Examples I, II and III have very long lasting ambery, fruity, ionone-like, winey, woody, sweet-woody aromas with urine-like top notes (desirable in perfumery) which may be utilized to a great extent in inexpensive functional products. The following pine/musk fragrance demonstrates the use of these materials in perfume compositions. In each of the cases the unsaturated branched-chain ketones are used in an amount of 47.9%:

| Ingredients | Parts by Weight Example | | |
|---|---|---|---|
| | IVA | IVB | IVC |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pumilionus | 50 | 50 | 50 |
| Eucalyptol | 50 | 50 | 50 |
| 2,2,6-trimethyl-1-cyclohexene-1-carboxaldehyde | 5 | 5 | 5 |
| Maltol 1% in Diethyl Phthalate | 5 | 5 | 5 |

EXAMPLE V

Preparation of a Cosmetic Powder

A cosmetic powder is prepared by mixing in a ball mill, 100 grams of talcum powder with 0.25 grams of one of the products listed below of our invention. The resulting material has an excellent perfume aroma as set forth in the table below:

TABLE II

| DESCRIPTION OF COMPOSITION | FRAGRANCE CHARACTERISTICS |
| --- | --- |
| A. Fragrance of Example IVA: | a piney aroma with ambery, fruity, ionone-like winey and woody nuances |
| B. Fragrance of Example IVB: | a piney aroma with sweet woody nuances and a faint pleasant animal-like top note |
| C. Fragrance of Example IVC: | a piney aroma with sweet woody nuances and a faint pleasant animal-like top note |
| D. Acetyl triisobutylene prepared according to Example I: | an ambery, fruity, ionone-like winey and woody aroma profile |
| E. Propionyl triisobutylene prepared according to Example II: | a sweet woody aroma profile with intense but pleasant animal-like nuances |
| F. Propionyl triisobutylene prepared according to Example III: | a sweet woody aroma profile with intense but pleasant animal-like nuances |

EXAMPLE VI

Perfumed Liquid Detergents

Concentrated liquid detergents with aromas as set forth in Table II of Example V, supra, (which detergents are produced from the Lysine salt of n-dodecyl benzene sulfonic acid, as more specifically described in U.S. Pat. No. 3,948,818, issued on Apr. 6, 1976) are prepared containing the perfume materials as set forth in Table II of Example V, supra. They are prepared by adding and homogeneously admixing the appropriate quantity of perfume material in the liquid detergent. The detergents all possess excellent aromas as set forth in Table II of Example V, supra.

EXAMPLE VII

Preparation of a Cologne and Handkerchief Perfume

Perfume compositions and substances as indicated in Table II of Example V, supra, are incorporated into colognes at concentrations of 1.5%, 2.0%, 2.5%, 3.0%, 3.5%, 4.0% and 5.0% in 80%, 85%, 90% and 95% aqueous food grade ethanol; and into handkerchief perfumes at concentrations of 10%, 15%, 20%, 30% 40% and 50% (in 90%, and 95% aqueous food grade ethanol). Distinct and definitive fragrance aromas as set forth in Table II of Example V, supra, are imparted to the colognes and to the handkerchief perfumes.

EXAMPLE VIII

Preparation of Soap Composition

One hundred grams of soap chips (obtained from Ivory ® Soap) (a trademark of Procter & Gamble Company of Cincinnati, Ohio) are mixed with two grams of each of the materials (separately) as set forth in Table II of Example V, supra, until a substantially homogeneous composition is obtained in each of the six cases. The resulting compositions are each individually melted at 180° C. for a periof of 4 hours under 8 atmospheres nitrogen pressure. The resulting melt are cooled and formed into soap bars. Each of the soap bars has an aroma as set forth in Table II of Example V, supra.

EXAMPLE IX

Preparation of Liquid Detergent

Concentrated liquid detergents with aromas as set forth in Table II of Example V, supra, containing 0.2%, 0.5% and 1.2% of the perfume composition and substances as set forth in Table II of Example V are prepared by adding the appropriate quantity of the indicated composition as set forth in Table II of Example V to a liquid detergent known as P-87. The aromas of the liquid detergent increase with increasing composition of the perfumery composition as set forth in Table II of Example V, supra.

EXAMPLE X

Utilizing the procedure of Example I of Column 15 of U.S. Pat. No. 3,632,396 (the disclosure and specification which is incorporated herein by reference) a nonwoven cloth substrate useful as a dryer-added fabric softening article of manufacture is prepared wherein the substrate, the substrate coating and the outer coating and the perfuming material are as follows:

1. a water "dissolve" paper ("Dissolvo Pager"):
2. Adogen 448 (m.p. about 140° F.) as the substrate coating; and
3. an outer coating having the following formulation (m.p. about 150° F.):
   57 percent $C_{20-22}$HAPS
   22 percent isopropyl alcohol
   20 percent antistatic agent 1 percent of a perfumery substance as set forth in Table II of Example V, supra, having aroma properties as set forth in Table II of Example V, supra.

Fabric-softening compositions prepared as set forth above having the aroma characteristics as set forth in Table II of Example V, supra, essentially consist of a substrate having the weight of about 3 grams per 100 square inches, a substrate coating of about 1.85 grams per 100 square inches of substrate, and an outer coating of about 1.4 grams per 100 square inches of substrate, thereby providing a total aromatized substrate and outer coating weight ratio of about 1:1 by weight of the substrate. The aromas as set forth in Table II of Example V, supra, are imparted in a pleasant manner to the head space in the dryer on operation thereof using the said dryer added fabric softening nonwoven fabric article.

EXAMPLE XI

Granular detergent compositions prepared according to United Kingdom Patent Specification No. 1,501,498 having the following formulas are prepared by spray-drying the following mixtures as indicated in the columns headed XIX A, XIX B, XIX C and XIX D:

| | COMPOSITION IN % BY WEIGHT | | | |
| --- | --- | --- | --- | --- |
| Ingredient | Example XIX$^A$ | Example XIX$^B$ | Example XIX$^C$ | Example XIX$^D$ |
| Sodium salt of ethoxylated fatty alcohol sulfate having an average of about 2.25 moles of ethylene oxide per mole of fatty alcohol[1] | 14.1 | 14.1 | 14.1 | 14.1 |
| Sodium tallow alkyl | 2.4 | 2.4 | 2.4 | 2.4 |

-continued

| Ingredient | Example XIX$^A$ | Example XIX$^B$ | Example XIX$^C$ | Example XIX$^D$ |
|---|---|---|---|---|
| sulfate | | | | |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |
| $Na_{12}(AlO_2.SiO_2)_{12}$ $27H_2O^2$ | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, brighteners | 4.0 | 2.4 | 3.6 | 2.3 |
| Fragrance material of Example IVA | 1.5 | 0.0 | 0.0 | 0.0 |
| Fragrance material of Example IVB | 0.0 | 2.0 | 0.0 | 0.0 |
| Fragrance material of Example IVC | 0.0 | 0.0 | 2.0 | 0.0 |
| Acetyl Triisobutylene prepared according to Example I | 0.0 | 0.0 | 0.0 | 3.0 |

[1] Fatty alcohol composition: 66% $C_{14}$:33% $C_{16}$:1% $C_{18}$.
[2] Prepared as described in United Kingdom Patent 1,501,498; average particle size diameter 2 microns.

Laundry solutions containing the above detergent compositions are used to launder fabrics. Each of the laundry compositions both prior to and on laundering gives rise to the following aromas:

| Description of Substance | Fragrance |
|---|---|
| A. Fragrance of Example IVA: | a piney aroma with ambery, fruity ionone-like winey and woody nuances |
| B. Fragrance of Example IVB: | a piney aroma with sweet woody nuances and a faint pleasant animal-like top note |
| C. Fragrance of Example IVC: | a piney aroma with sweet woody nuances and a faint pleasant animal-like top note |
| D. Acetyl triisobutylene prepared according to Example I: | an ambery, fruity, ionone-like winey and woody aroma profile |

EXAMPLE X

Perfumed Liquid Detergent

Concentrated liquid detergents having aromas as set forth in Table II of Example V, supra, are prepared containing 0.10%, 0.15%, 0.20%, 0.40% and 0.80% of one of the materials as set forth in Table II of Example V, supra. They are prepared by adding and homogeneously mixing the appropriate quantity of mixture of perfume materials in the liquid detergent. The liquid detergent is a builder-free liquid detergent consisting of (a) 50% of a non-ionic surfactant having an HLB of 8.0 and a critical micelle concentration of 0.007 weight percent at 25° C.; (b) an ionic surfactant which is triethanolamine citrate; and (c) one weight percent of diethanolamine prepared according to United Kingdom Patent Specification No. 1,491,603.

The detergents all posses fragrances as set forth in Table II of Example V, the intensity increasing with greater concentrations of fragrance material:

| Description of Substance | Fragrance |
|---|---|
| A. Fragrance of Example IVA: | a piney aroma with ambery, fruity ionone-like winey and woody nuances |
| B. Fragrance of Example IVB: | a piney aroma with sweet woody nuances and a faint pleasant animal-like top note |
| C. Fragrance of Example IVC: | a piney aroma with sweet woody nuances and a faint pleasant animal-like top note |
| D. Acetyl triisobutylene prepared according to Example I: | an ambery, fruity, ionone-like winey and woody aroma profile |

What is claimed is:

1. A process for augmenting or enhancing the aroma of a fabric softener composition or a drier-added fabric softener article comprising the step of adding to a drier-added fabric softener article component or a fabric softener composition, an aroma augmenting or enhancing quantity of a product prepared by the process of (a) trimerizing isobutylene to form triisobutylene, a mixture of substances defined according to the structures:

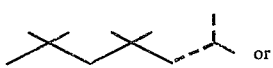 or

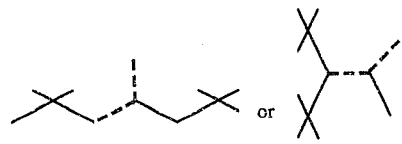

wherein in each of the molecules one of the dashed lines is a carbon-carbon double bond and the other of the dashed lines is a carbon-carbon single bond and (b) reacting the resulting triisobutylene composition of matter with an alkanoic acid anhydride having the structure:

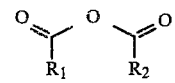

wherein $R_1$ and $R_2$ are the same or different and are each selected from the group consisting of methyl and ethyl, in the presence of a Lewis acid catalyst thereby producing a mixture of compounds comprising the compounds defined according to the structures:

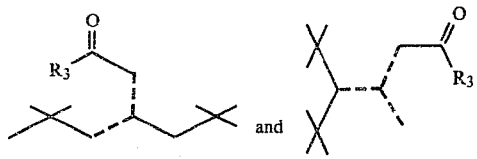

wherein $R_3$ represents methyl or ethyl and in each of the molecules one of the dashed lines represents a carbon-carbon double bond and each of the other of the dashed lines represents a carbon-carbon single bond.

* * * * *